US010655161B2

(12) United States Patent
Yeh

(10) Patent No.: US 10,655,161 B2
(45) Date of Patent: May 19, 2020

(54) DIAGNOSTIC AND PROGNOSTIC ASSAYS BASED ON CIRCULATING TYROSINE KINASE ACTIVITY

(71) Applicant: Quest Diagnostics Investments Incorporated, Wilmington, DE (US)

(72) Inventor: Chen-Hsiung Yeh, Arcadia, CA (US)

(73) Assignee: Quest Diagnostics Investments Incorporated, Wilmington, DE (US)

( * ) Notice: Subject to any disclaimer, the term of this patent is extended or adjusted under 35 U.S.C. 154(b) by 338 days.

(21) Appl. No.: 14/558,987

(22) Filed: Dec. 3, 2014

(65) Prior Publication Data

US 2015/0184222 A1 Jul. 2, 2015

Related U.S. Application Data

(63) Continuation of application No. 13/286,867, filed on Nov. 1, 2011, now Pat. No. 8,921,062.

(60) Provisional application No. 61/411,651, filed on Nov. 9, 2010.

(51) Int. Cl.
C12Q 1/48 (2006.01)
G01N 33/574 (2006.01)

(52) U.S. Cl.
CPC ....... *C12Q 1/485* (2013.01); *G01N 33/57426* (2013.01); *G01N 33/57488* (2013.01); *G01N 2800/52* (2013.01)

(58) Field of Classification Search
CPC .................................................. C12N 9/12
USPC ....................................................... 435/194
See application file for complete search history.

(56) References Cited

U.S. PATENT DOCUMENTS 5,817,765 A 10/1998 Isaksson et al.

OTHER PUBLICATIONS

Scheufler et al, Implications of Vascular Endothelial Growth Factor, sFlt-1, and sTie-2 in Plasma, Serum and Cerebrospinal Fluid During Cerebral Ischemia in Man. J Cereb Blood Flow Metab, vol. 23, No. 1, 2003 p. 99-110.*
Huang et al, Detection of Chromosome Translocations by Bead-Based Flow Cytometry. In: Monoclonal antibodies: methods and protocols. Methods in molecular biology. Clifton, NJ: Humana Press; 2007. Chapter 12, p. 167-174.*
Samayawardhena et al, PTPa Activates Lyn and Fyn and Suppresses Hck to Negatively Regulate Fc«RI-Dependent Mast Cell Activation and Allergic Responses. J Immunol 2010; 185:5993-6002; Prepublished online Oct. 13, 2010.*
Lee et al, Serum Tyrosine Kinase Activity and Neoplastic Disease. Recent Results in Cancer Research, vol. 113, 1989, p. 32-40*
Lin et al, Characterization of tyrosyl kinase activity in human serum. J Biol Chem. Feb. 10, 1985;260(3):1582-7.*
GenWay, Inc. Universal Tyrosine Kinase Assay Kit p. 1-11. Downloaded Jan. 9, 2017.*
Gambacorti-Passerini et al, Differences between in Vivo and in Vitro Sensitivity to Imatinib of Bcr/Abl_ Cells Obtained from Leukemic Patients. Blood Cells, Molecules, and Diseases (2002) 28(3) May/June: 361-372.*
Wu et al, Assaying Bcr-Abl kinase activity and inhibition in whole cell extracts by phosphorylation of substrates immobilized on agarose beads. Analytical Biochemistry 347 (2005) 67-76.*
Lugo et al, Tyrosine kinase activity and transformation potency of bcr-abl oncogene products.. Science. Mar. 2, 1990;247(4946):1079-82.*
Jilani et al, An immunological method for the detection of BCR-ABL fusion protein and monitoring its activation. Leukemia Research 32 (2008) 936-943.*
Cohn et al., Preparation and properties of serum and plasma proteins. III. Size and charge of proteins separating upon equilibration across membranes with ethanol-water mixtures of controlled pH, ionic strength and temperature. Am. Chem. Soc., (1940), 62:3396-3400.
Cohn et al., A system for the separation of the components of human blood: Quantitative procedures for the separation of the protein components of human plasma. J. Am. Chem. Soc., (1950), 72:465-474.
Dewar et al., Macrophage colony stimulating factor receptor, c-fms, is a novel target of imatinib. Blood. (2005), 105:3127-3132.
Druker BJ. STI571 (GleevecTM ) as a paradigm for cancer therapy. Trends Mol Med (2002) 8:S14-S18.
Druker positive cells, "Effects of a selective inhibitor of the Abl tyrosine kinase on the growth of Bcr-Abl positive cells," Nat Med., (1996), 2(5):561-566.
Druker et al., "Five-Year Follow-up of Patients Receiving Imatinib for Chronic Myeloid Leukemia," N Eng J Med., (2006), 355(23):2408-2417.
Fotino et al., Micromethod for Rapid Separation of Lymphocytes from Peripheral Blood, Ann. Clin. Lab. Sci., (1971), 1(2):131-133.
Giles et al., "A prognostic model for survival in chronic lymphocytic leukaemia based on p53 expression," British Journal of Hemotology, (2003), 121:578-585.
Jilani et al., Phosphorylation levels of BCR-ABL, CrkL, AKT and STAT5 in imatinib-resistant chronic myeloid leukemia cells implicate alternative pathway usage as a survival strategy. Leukemia Res (2008) 32:643-649.
Krause DS, Van Etten RA, Tyrosine kinases as targets for cancer therapy, N Engl J Med, (2005), 353:172-187.
Lee et al., "BCR-ABL alternative splicing as a common mechanism for imatinib resistance: evidence from molecular dynamics simulations," Mol Cancer Ther., (2008), 7(12):3834-3841.

(Continued)

*Primary Examiner* — Sheridan Swope
(74) *Attorney, Agent, or Firm* — Foley & Lardner LLP

(57) ABSTRACT

Provided herein are methods for the diagnosis, prognosis, or management of diseases, such as cancer, by measuring the tyrosine kinase activity in acellular body fluids. Further provided are methods of predicting response to therapy in certain populations of cancer patients by contacting an acellular body fluid sample from a patient with a test agent, such as a tyrosine kinase inhibitor, and then measuring the effect of the test agent on tyrosine kinase activity in the sample.

5 Claims, 3 Drawing Sheets

(56) References Cited

OTHER PUBLICATIONS

Ma et al., "BCR-ABL Truncation due to Premature Translation Termination as a Mechanism of Resistance to Kinase Inhibitors," Acta Haematol., (2009), 121:27-31.
Ma et al., "Plasma RNA as an alternative to cells for monitoring moelcular response in patients with chronic myeloid leukemia," Haematol., (2007), 92(2):170-175.
Marcucci et al., "Molecular heterogeneity and prognostic biomarkers in adults with acute myeloid leukemia and normal cytogenetics," Curr. Opin. Hematol., (2005), 12(1):68-75.
McGary et al., Imatinib mesylate inhibits platelet-derived growth factor receptor phosphorylation of melanoma cells but does not affect tumorigenicity in vivo. J Invest Dermatol 2004;122:400-405.
Ocana A, et al, Novel tyrosine kinase inhibitors in the treatment of cancer, Current Drug Targets,(2009), 10:575-576.
Okuda et al., "ARG tyrosine kinase activity is inhibited by ST1571," Blood, (2001), 97:2440-2448.
Peng et al., "Pharmacokinetics and Pharmacodynamics of Imatinib in a Phase I Trial With Chronic Myeloid Leukemia Patients," J Clin Oncol., (2004), 22(5):935-942.
Pennel, R.B., "Fractionation and isolation of purified components by precipitation methods," The Plasma Proteins, vol. 1, Chapter 2, F.W. Putman (ed). Academic Press, New York, (1960), 9-50.
Rickwood et al., "Nycodenz: A New Nonionic Iodinated Gradient Medium," Anal. Biochem., (1982), 123:23-31.
Schlessinger et al., "Nuclear Signaling by Receptor Tyrosine Kinases: The First Robin of Spring," Cell, (2006), 127:45-48.
Schlessinger J., "Cell Signaling by Receptor Tyrosine Kinases," Cell, (2000), 103:211-225.
Schlessinger J., "Signal transduction. Autoinhibition control," Science, (2003), 300:750-752.
Shah et al., "Overriding Imatinib Resistance with a Novel ABL Kinase Inhibitor," Science, (2004), 305:399-401.
Talpaz et al., "Dasatinib in Imatinib-Resistant Philadelphia Chromosome-Positive Leukemias," N Eng J Med., (2006), 354(24):2531-2541.
Vlahovic et al., "Activation of Tyrosine Kinases in Cancer," The Oncologist, (2003), 8:531-538.
White et al., "In vitro sensitivity to imatinib-induced inhibition of ABL kinase activity is predictive of molecular response in patients with de novo CML," Blood, (2005), 106:2520-2526.
Wong and Witte, The BCR-ABL story: Bench to bedside and back. Annual Rev Immunol., (2004), 22:247-306.
Zhang et al., "Targeting cancer with small molecule kinase inhibitors," Nat. Rev. Cancer, (2009), 9:28-39.
Haas et al., "Detection of a Tyrosine Kinase in Human Sera and Blood Cells by PP-60-SRC Antiserum," Biochemical and Biophysical Research Communications, vol. 135, No. 2, pp. 426-434, 1986.
Lin et al., "Developmental Expression of Tyrosyl Kinase Activity in Human Serum," Human Biology, vol. 59, No. 3, 549-556, 1987.
Braunwalder et al., "A Solid-Phase Assay for the Determination of Protein Tyrosine Kinase Activity of c-src Using Scintillating Microtitration Plates," Analytical Biochemistry, vol. 234, pp. 23-26, 1996.
Jilani et al., "Measurement of free circulating Bcr-Abl fusion protein and its pbosphorylation in patients with chronic myeloid leukemia," Blood, vol. 106, No. 11, p. 568A, Nov. 16, 2005.
Office Action dated Feb. 5, 2013 in U.S. Appl. No. 13/286,867.
Office Action dated Sep. 6, 2013 in U.S. Appl. No. 13/286,867.
Office Action dated Dec. 30, 2013 in U.S. Appl. No. 13/286,867.
Office Action dated Apr. 22, 2014 in U.S. Appl. No. 13/286,867.
Notice of Allowance dated Aug. 22, 2014 in U.S. Appl. No. 13/286,867.

* cited by examiner

DIAGNOSTIC AND PROGNOSTIC ASSAYS BASED ON CIRCULATING TYROSINE KINASE ACTIVITY

CROSS-REFERENCE TO RELATED APPLICATIONS

This application is a continuation of U.S. patent application Ser. No. 13/286,867, filed Nov. 1, 2011, now U.S. Pat. No. 8,921,062, issued on Dec. 30, 2014, which claims benefit of U.S. Provisional application 61/411,651, filed Nov. 9, 2010, which is hereby incorporated by reference in its entirety.

FIELD OF THE INVENTION

The invention relates to the diagnosis, prognosis, and management of disease, including cancer.

BACKGROUND OF THE INVENTION

The following discussion of the background of the invention is merely provided to aid the reader in understanding the invention and is not admitted to describe or constitute prior art to the present invention.

Tyrosine kinases (TKs) play a central role in cellular signaling networks, acting as relay points for multiple interdependent pathways that initiate from cell surface receptors and ultimately converge on gene expression within the nucleus. Delicate regulation of TK activity controls diverse cellular homeostatic mechanisms, such as the cell cycle, proliferation, differentiation, motility, and apoptosis or survival. TK activity is tightly regulated in normal cells but mutation(s), overexpression of TK, or aberrant autocrine activation may cause constitutive activation leading to malignancy. Consequently, TKs have emerged as clinically attractive target molecules for drug development.

Targeted TK inhibitors (TKIs) for cancer treatment represent a breakthrough in innovative intervention strategies. As TKIs become more widely used in clinical practice, it will be critical to identify subpopulations of patients who will respond to these therapies. However, the identification of potential TKI responders is not straightforward, as demonstrated by results of preclinical data with small molecule inhibitors, the complex nature of TK activation, and the lack of a standardized assay for measuring TK levels or activity in tumors.

Constitutive BCR-ABL1 TK activation and downstream signaling represent the pathogenetic hallmarks of chronic myelogenous leukemia (CML), and selective ABL1 TKI therapy has revolutionized the management of this disease. Three such selective TKIs are currently approved for treatment of CML and BCR-ABL1-positive (i.e., Philadelphia chromosome-positive) ALL: imatinib, nilotinib, and dasatinib. The clinical efficacy of imatinib, a selective ABL1 kinase inhibitor and the next generation more potent nilotinib, have been demonstrated in all phases of CML. However, the development of drug resistance constitutes a major drawback in the treatment of advanced-phase disease. Dasatinib, a highly potent dual inhibitor of ABL1 and Src, is recently approved by FDA for first-line therapy in CML patients who do not respond well to imatinib, even though dasatinib still has its own shortcoming and is not effective for certain subclass of resistant patients. Assays are needed to assist the physician in the appropriate diagnosis and selection of therapy for CML and ALL patients.

SUMMARY OF THE INVENTION

The present invention is based on the discovery that circulating tyrosine kinase activity may be detected in patient samples and that such activity can have clinical value in the diagnosis and prognosis of certain disease states.

In one aspect, the present invention provides a method for identifying the presence of absence of (i.e., diagnosing) neoplastic disease in a subject, the method comprising: determining, in an acellular body fluid sample from the subject, the activity level of one or more circulating tyrosine kinases (cTK), and (a) identifying the subject as having a neoplastic disease when the activity level of one or more circulating tyrosine kinases is different when compared to a reference activity level and (b) identifying the subject as not having a neoplastic disease when the activity level of the one or more circulating tyrosine kinases is not different compared to a reference activity level. In one embodiment, the acellular body fluid is selected from the group consisting of serum and plasma.

In one embodiment, the neoplastic disease is a proliferative hematological disorder. In one embodiment, the proliferative hematological disorder is selected from the group consisting of chronic myelogenous leukemia (CML), chronic lymphocytic leukemia (CLL), acute myeloid leukemia (AML), myelodysplastic syndrome (MDS), and acute lymphoblastic leukemia (ALL). In one embodiment, the proliferative hematological disorder is chronic myelogenous leukemia (CML) or acute lymphoblastic leukemia (ALL).

In one embodiment, the reference activity level is a value determined from the cTK activity present in a comparable sample from healthy individuals, and an increase or decrease in the subject's cTK activity level relative to the reference level is used to determine a diagnosis for the subject. In one embodiment, a cTK activity level in the subject sample that is higher than a reference activity level indicates a diagnosis of chronic myelogenous leukemia (CML) for the subject. In one embodiment, a cTK activity level in the subject sample that is higher than a reference activity level indicates a diagnosis of BCR-ABL1-positive acute lymphocytic leukemia (ALL) for the subject.

In one embodiment, the determining comprises (a) contacting the sample from the subject with one or more substrates for a tyrosine kinase; (b) measuring the phosphorylation of the one or more substrates by the circulating tyrosine kinases in the sample to determine the activity level of the one or more circulating tyrosine kinases. In one embodiment, the one or more substrates is a universal tyrosine kinase substrate peptide. In one embodiment, the universal tyrosine kinase substrate peptide is Poly(Glu-Tyr). In one embodiment, measuring the phosphorylation of the one or more substrates is by contacting the substrates with a phospho-tyrosine-specific antibody. In one embodiment, the phospho-tyrosine-specific antibody is detectably labeled.

In another aspect, the present invention provides a method for predicting patient response to therapy comprising: (a) measuring a first level of cTK activity in a first body fluid sample (e.g., serum or plasma) from a patient; (b) contacting a second body fluid sample from the patient with an effective amount of one or more test agents; (c) measuring a second level of cTK activity in the second body fluid sample after it has been contacted with the one or more test agents; and (d) comparing the first level to the second level, wherein a decrease between the first level and the second level indicates that the patient is a potential responder to therapy with the one or more test agents and wherein no change between the first level and the second level indicates that the patient is a potentially not a responder to therapy with the one or more test agents.

In one embodiment, the patient is diagnosed as having a proliferative hematological disorder. Some embodiments, the proliferative hematological disorder is selected from the group consisting of chronic myelogenous leukemia (CML), chronic lymphocytic leukemia (CLL), acute myeloid leukemia (AML), myelodysplastic syndrome (MDS), and acute lymphoblastic leukemia (ALL). In one embodiment, the proliferative hematological disorder is chronic myelogenous leukemia (CML) or acute lymphoblastic leukemia (ALL).

In one embodiment, the one or more substrates is a universal tyrosine kinase substrate peptide. In one embodiment, the universal tyrosine kinase substrate peptide is Poly(Glu-Tyr). In one embodiment, measuring the phosphorylation of the one or more substrates is by contacting the substrates with a phospho-tyrosine-specific antibody. In one embodiment, the phospho-tyrosine-specific antibody is detectably labeled.

In one embodiment, the one or more test agents are tyrosine kinase inhibitors. In one embodiment, the one or more test agents are selected from the group consisting of: imatinib, nilotinib, and dasatinib.

In another aspect, the present invention provides a kit for assaying circulating tyrosine kinase activity comprising: (i) a universal tyrosine kinase substrate peptide; (ii) a phospho-tyrosine-specific antibody; and (iii) reagents for the preparation of serum or plasma samples. In one embodiment, the kit further comprises a container suitable for the assay of serum or plasma samples. In one embodiment, the kit further comprises a series of standard solutions having a known amount of circulating tyrosine kinase activity.

In one embodiment, the kit further comprises one or more test agents. In one embodiment, the one or more test agents are selected from the group consisting of: imatinib, nilotinib, and dasatinib.

In another aspect, the present invention provides a method for monitoring effectiveness of treatment by (a) measuring a first activity level of one or more circulating tyrosine kinases (cTK) in a first body fluid sample collected from a patient before initiation of treatment; (b) measuring a second activity level of one or more circulating tyrosine kinases (cTK) in a second body fluid sample collected after initiation of treatment; and (c) comparing the second level to the first level, wherein a decrease between the second level and the first level indicates that the patient is responding to treatment and wherein a lack of change or increase between the second level and the first level indicates that the patient is not responding to treatment.

In another aspect, the present invention provides a method for determining patient prognosis by (a) measuring a first level of cTK activity in a first body fluid sample collected at a first time from a patient; (b) measuring a second level of cTK activity in a second body fluid sample collected at a second time from said patient; and (c) comparing the first level to the second level, wherein a decrease between the first level and the second level indicates that the patient has a good prognosis and lack of a decrease between the first level and the second level indicates that the patient has a poor prognosis.

In another aspect, the present invention provides a method for determining patient prognosis by (a) determining, in an acellular body fluid sample from the patient, the activity level of one or more circulating tyrosine kinases (cTK); (b) comparing the sample activity level to a reference activity level; and, (c) identifying the patient as having a favorable prognosis when the sample activity level is (i) unchanged from a reference activity level that corresponds to comparable samples from healthy individuals or to levels known to correspond with favorable outcomes or (ii) different from a reference activity level that corresponds to comparable samples from diseased individuals or to levels known to correspond with unfavorable outcomes; and, (d) identifying the patient as having an unfavorable prognosis when the sample activity level is (i) different from a reference activity level that corresponds to comparable samples from healthy individuals or to levels known to correspond with favorable outcomes or (ii) unchanged from a reference activity level that corresponds to comparable samples from diseased individuals or to levels known to correspond with unfavorable outcomes.

In another aspect, the present invention provides a method for identifying a cTK modulator, said method comprising: contacting an acellular body fluid sample from a patient and determining the test compound's ability to modulate the activity of a cTK, wherein a change in cTK activity indicates a cTK modulator.

BRIEF DESCRIPTION OF THE FIGURES

FIG. 2A. Plasma samples from a newly diagnosed and a multidrug-resistant CML patient (T315I mutation) were incubated with imatinib (1.0, 5.0, 10, and 25 µM) or dasatinib (50, 100, and 1,000 nM) at physiologically relevant concentrations. Circulating TK activity was then measured. FIG. 2B. Dependence of drug resistance on expression level of BCR-ABL1 35-nt INS mutant in ex vivo circulating TK (cTK) activity assay. Plasma samples from drug-resistant CML patients expressing 10% or 35% 35-nt INS mutant BCR-ABL1 mRNA were incubated with imatinib (1.0, 5.0, 10, and 25 µM) or dasatinib (50, 100, and 1,000 nM) at physiologically relevant concentrations followed by measurement of cTK activity. All data are expressed as percent inhibition relative to the no-drug baseline.

DETAILED DESCRIPTION OF THE INVENTION

Figure 1A:
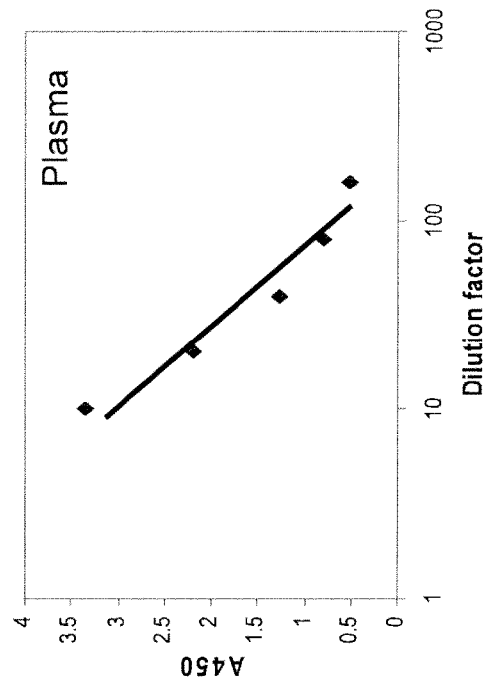
FIGS. 1A-1C show that circulating TK activity is readily detectable in human plasma and serum. The panels show the representative linearity curves of kinase activity vs. sample concentration for (A) K562 lysate, (B) plasma, and (C) serum samples. Serial dilutions of different samples were subjected to TK activity measurement by spectrophotometry at an absorbance of 450 nm.

The present invention relates generally to methods of assessing tyrosine kinase activity in acellular body fluids for the diagnosis of disease. As demonstrated herein, increasing or decreasing amounts of the activity of one or more circulating tyrosine kinases (cTK) correlates with the presence of disease or the prognosis of a patient suffering from a disease. In particular, methods for diagnosing neoplastic diseases, determining the likelihood of survival, and methods for predicting likelihood for responsiveness to therapy are provided. In some embodiments, cTK activity is significantly higher in plasma of patients with BCR-ABL1-positive leukemia. Ex vivo assays measuring the effect of therapeutic agents on plasma cTK activity may be used as drug sensitivity tests for predicting and monitoring response to specific agents.

The present technology is described herein using several definitions, as set forth throughout the specification. As used herein, unless otherwise stated, the singular forms "a," "an," and "the" include plural reference. Thus, for example, a reference to "a tyrosine kinase" is a reference to one or more tyrosine kinases.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the enumerated value.

The terms "assessing" and "evaluating" are used interchangeably to refer to any form of measurement, and include determining if a characteristic, trait, or feature is present or not. The terms "determining," "measuring," "assessing," and "assaying" are used interchangeably and include both quantitative and qualitative determinations. Assessing may be relative or absolute. "Assessing the presence of" includes determining the amount of something present, as well as determining whether it is present or absent.

The term "body fluid" or "bodily fluid" as used herein refers to any fluid from the body of an animal. Examples of body fluids include, but are not limited to, plasma, serum, blood, lymphatic fluid, cerebrospinal fluid, synovial fluid, urine, saliva, mucous, phlegm and sputum. A body fluid sample may be collected by any suitable method. The body fluid sample may be used immediately or may be stored for later use. Any suitable storage method known in the art may be used to store the body fluid sample; for example, the sample may be frozen at about −20° C. to about −70° C. Suitable body fluids are acellular fluids. "Acellular" fluids include body fluid samples in which cells are absent or are present in such low amounts that the kinase activity level determined reflects its level in the liquid portion of the sample, rather than in the cellular portion. Typically, an acellular body fluid contains no intact cells. Examples of acellular fluids include plasma or serum, or body fluids from which cells have been removed.

The term "clinical factors" as used herein, refers to any data that a medical practitioner may consider in determining a diagnosis or prognosis of disease. Such factors include, but are not limited to, the patient's medical history, a physical examination of the patient, complete blood count, examination of blood cells or bone marrow cells, cytogenetics, and immunophenotyping of blood cells. Activity of one or more circulating tyrosine kinases is a clinical factor.

The term "comparable" or "corresponding" in the context of comparing two or more samples, means that the same type of sample (e.g., plasma) is used in the comparison. For example, an activity level of one or more circulating tyrosine kinases in a sample of plasma can be compared to an activity level in another plasma sample. In some embodiments, comparable samples may be obtained from the same individual at different times. In other embodiments, comparable samples may be obtained from different individuals (e.g., a patient and a healthy individual). In general, comparable samples are normalized by a common factor. For example, acellular body fluid samples are typically normalized by volume body fluid and cell-containing samples are normalized by protein content or cell count.

As used herein, the term "diagnosis" means detecting a disease or disorder or determining the stage or degree of a disease or disorder. Usually, a diagnosis of a disease or disorder is based on the evaluation of one or more factors and/or symptoms that are indicative of the disease. That is, a diagnosis can be made based on the presence, absence or amount of a factor which is indicative of presence or absence of the disease or condition. Each factor or symptom that is considered to be indicative for the diagnosis of a particular disease does not need be exclusively related to the particular disease; i.e. there may be differential diagnoses that can be inferred from a diagnostic factor or symptom. Likewise, there may be instances where a factor or symptom that is indicative of a particular disease is present in an individual that does not have the particular disease. The term "diagnosis" also encompasses determining the therapeutic effect of a drug therapy, or predicting the pattern of response to a drug therapy. The diagnostic methods may be used independently, or in combination with other diagnosing and/or staging methods known in the medical art for a particular disease or disorder, e.g., a neoplastic disease.

As used herein, the phrase "difference of the level" refers to differences in the quantity of a particular marker, such as a protein or protein activity, in a sample as compared to a control or reference level. For example, the quantity of particular protein and/or the amount of a protein activity may be present at an elevated amount or at a decreased amount in samples of patients with a neoplastic disease compared to a reference level. In one embodiment, a "difference of a level" may be a difference between the activity of one or more circulating tyrosine kinases present in a sample as compared to a control of at least about 1%, at least about 2%, at least about 3%, at least about 5%, at least about 10%, at least about 15%, at least about 20%, at least about 25%, at least about 30%, at least about 35%, at least about 40%, at least about 50%, at least about 60%, at least about 75%, at least about 80% or more. In one embodiment, a "difference of a level" may be a statistically significant difference between the activity of one or more circulating tyrosine kinases present in a sample as compared to a control. For example, a difference may be statistically significant if the measured level of the kinase activity falls outside of about 1.0 standard deviations, about 1.5 standard deviations, about 2.0 standard deviations, or about 2.5 stand deviations of the mean of any control or reference group.

As used herein, the term "kinase" includes a protein that is capable of modulating its own phosphorylation state or the phosphorylation state of a different protein, polypeptide, or other non-proteinaceous molecule. A "tyrosine kinase" is a protein that phosphorylates a protein or polypeptide on a tyrosine amino acid.

The term "label" as used herein, refers to any physical molecule directly or indirectly associated with a specific binding agent or antigen which provides a means for detection for that antibody or antigen. A "detectable label" as used herein refers any moiety used to achieve signal to measure the amount of complex formation between a target and a binding agent. These labels are detectable by spectroscopic, photochemical, biochemical, immunochemical, electromagnetic, radiochemical, or chemical means, such as fluorescence, chemifluoresence, or chemiluminescence, electrochemiluminescence or any other appropriate means. Suitable detectable labels include fluorescent dye molecules or fluorophores.

The term "neoplastic diseases" as used herein refers to cancers of any kind and origin and precursor stages thereof. Accordingly, the term "neoplastic disease" includes the subject matter identified by the terms "neoplasia", "neoplasm", "cancer", "pre-cancer" or "tumor". A neoplastic disease is generally manifest by abnormal cell division resulting in an abnormal level of a particular cell population. The abnormal cell division underlying a neoplastic disease is typically inherent in the cells and not a normal physiological response to infection or inflammation.

The term "prognosis" as used herein refers to a prediction of the probable course and outcome of a clinical condition or disease. A prognosis is usually made by evaluating factors or symptoms of a disease that are indicative of a favorable or unfavorable course or outcome of the disease. The phrase "determining the prognosis" as used herein refers to the process by which the skilled artisan can predict the course or outcome of a condition in a patient. The term "prognosis" does not refer to the ability to predict the course or outcome of a condition with 100% accuracy. Instead, the skilled artisan will understand that the term "prognosis" refers to an increased probability that a certain course or outcome will occur; that is, that a course or outcome is more likely to occur in a patient exhibiting a given condition, when compared to those individuals not exhibiting the condition.

The terms "favorable prognosis" and "positive prognosis," or "unfavorable prognosis" and "negative prognosis" as used herein are relative terms for the prediction of the probable course and/or likely outcome of a condition or a disease. A favorable or positive prognosis predicts a better outcome for a condition than an unfavorable or negative prognosis. In a general sense, a "favorable prognosis" is an outcome that is relatively better than many other possible prognoses that could be associated with a particular condition, whereas an unfavorable prognosis predicts an outcome that is relatively worse than many other possible prognoses that could be associated with a particular condition. Typical examples of a favorable or positive prognosis include a better than average cure rate, a lower propensity for metastasis, a longer than expected life expectancy, differentiation of a benign process from a cancerous process, and the like. For example, a positive prognosis is one where a patient has a 50% probability of being cured of a particular cancer after treatment, while the average patient with the same cancer has only a 25% probability of being cured.

The term "proliferative hematological disorder" as used herein means a disorder of a bone marrow or lymph node-derived cell type, such as a white blood cell. A proliferative hematological disorder is generally manifest by abnormal cell division resulting in an abnormal level of a particular hematological cell population. The abnormal cell division underlying a proliferative hematological disorder is typically inherent in the cells and not a normal physiological response to infection or inflammation. A leukemia is a type of proliferative hematological disorder. Exemplary proliferative hematological disorders include, but are not limited to, acute myeloid leukemia, acute lymphoblastic leukemia, chronic lymphocytic leukemia, myelodysplastic syndrome, chronic myeloid leukemia, hairy cell leukemia, leukemic manifestations of lymphomas, and multiple myeloma. Lymphoma is a type of proliferative disease that mainly involves lymphoid organs, such as lymph nodes, liver, and spleen. Exemplary proliferative lymphoid disorders include lymphocytic lymphoma (also called chronic lymphocytic leukemia), follicular lymphoma, large cell lymphoma, Burkitt's lymphoma, marginal zone lymphoma, lymphoblastic lymphoma (also called acute lymphoblastic lymphoma).

As used herein, "plasma" refers to acellular fluid found in blood. Plasma may be obtained from blood by removing whole cellular material from blood by methods known in the art (e.g., centrifugation, filtration, and the like). As used herein, "peripheral blood plasma" refers to plasma obtained from peripheral blood samples.

As used herein, "serum" includes the fraction of plasma obtained after plasma or blood is permitted to clot and the clotted fraction is removed.

As used herein, the term "reference level" refers to a level of a substance which may be of interest for comparative purposes. In one embodiment, a reference level may be the activity level of one or more circulating tyrosine kinases expressed as an average of the level of the one or more circulating tyrosine kinases from samples taken from a control population of healthy (disease-free) subjects. In another embodiment, the reference level may be the level in the same subject at a different time, e.g., before the present assay such as the level determined prior to the subject developing the disease or prior to initiating therapy. In general, samples are normalized by a common factor. For example, acellular body fluid samples are normalized by volume body fluid and cell-containing samples are normalized by protein content or cell count.

As used herein, the term "sample" may include, but is not limited to, bodily tissue or a bodily fluid such as blood (or a fraction of blood such as plasma or serum), lymph, mucus, tears, saliva, sputum, urine, semen, stool, CSF, ascites fluid, or whole blood, and including biopsy samples of body tissue. A sample may be obtained from any subject, e.g., a subject/patient having or suspected to have a neoplastic disease.

As used herein, the term "subject" refers to a mammal, such as a human, but can also be another animal such as a domestic animal (e.g., a dog, cat, or the like), a farm animal (e.g., a cow, a sheep, a pig, a horse, or the like) or a laboratory animal (e.g., a monkey, a rat, a mouse, a rabbit, a guinea pig, or the like). The term "patient" refers to a "subject" who is, or is suspected to be, afflicted with a neoplastic disease.

Overview

Disclosed herein are methods for detecting the presence or absence of disease in subjects based, at least in part, on results of testing methods of the present technology on a sample. Further disclosed herein are methods for monitoring the status of subjects diagnosed with neoplastic diseases based at least partially on results of tests on a sample. The test samples disclosed herein are represented by, but not limited in anyway to, blood or a fraction of blood such as plasma, serum, or particular cell fractions. This disclosure is drawn, inter alia, to methods of diagnosing and monitoring neoplastic diseases using measurements of circulating tyrosine kinase (cTK) activity.

The present inventors have discovered that analyzing cTK activity can provide a profile that may be used for classifying and stratifying cancer patients for diagnosis, therapy, and prediction of clinical behavior. In the context of cancer diagnosis, it is frequently difficult to have access to the diseased cells. This is true even in hematologic diseases because of the problem of dilution effects by normal cells. In various embodiments, the present methods overcome problems of cancer diagnosis by determining the levels of cTK activities in the plasma or serum of patients with proliferative hematological disorders. Traditional techniques such as sequencing, FISH, immunohistochemistry, and ELISA can detect genetic mutations or measure levels of expression and phosphorylation/activation of various signaling molecules. However, activity-based assays are preferable in terms of direct functional detection of the drug target (i.e., TK) before or after treatment. The inventive assays provide a simple, direct, accurate, and reliable TK activity assay for use in evaluating the response to certain TKIs and for monitoring drug efficacy during therapy.

In one aspect, the methods generally provide for the detection, measuring, and comparison of a pattern of cTK activity in a patient sample. Additional diagnostic markers may be combined with the cTK activity to construct models for predicting the presence or absence or stage of a disease. For example, clinical factors of relevance to the diagnosis of neoplastic diseases, include, but are not limited to, the patient's medical history, a physical examination, complete blood count, and other markers. In one embodiment, the methods additionally detect the presence or absence of a BCR-ABL1 mutation. In one embodiment, the methods additionally detect the expression level of BCR-ABL1. In one embodiment, the methods additionally detect CRKL and/or STAT-5 phosphorylation.

Accordingly, the various aspects relate to the collection, preparation, separation, identification, characterization, and comparison of the cTK activity in a test sample. The technology is useful, alone or in combination with additional biomarkers, to determine the presence or absence of a neoplastic disease or any progressive state thereof. The technology is also useful to test the sensitivity of the cTK proteins in a patient sample to a therapeutic agent in order to ascertain whether that agent may be efficacious in treating the patient's condition.

Sample Preparation

Test samples of acellular body fluid or cell-containing samples may be obtained from an individual or patient. Methods of obtaining test samples are well-known to those of skill in the art and include, but are not limited to, aspirations or drawing of blood or other fluids. Samples may include, but are not limited to, whole blood, serum, plasma, saliva, cerebrospinal fluid (CSF), pericardial fluid, pleural fluid, urine, and eye fluid.

In embodiments in which the cTK activity will be determined using an acellular body fluid, the test sample may be a cell-containing liquid or an acellular body fluid (e.g., plasma or serum). In some embodiments in which the test sample contains cells, the cells may be removed from the liquid portion of the sample by methods known in the art (e.g., centrifugation) to yield acellular body fluid for the cTK activity measurement. In suitable embodiments, serum or plasma are used as the acellular body fluid sample. Plasma and serum can be prepared from whole blood using suitable methods well-known in the art. In these embodiments, data may be normalized by volume of acellular body fluid.

In some embodiments, the cTK activity is determined using a cell-containing sample. In these embodiments, the cell-containing sample includes, but is not limited to, blood, urine, organ, and tissue samples. In suitable embodiments, the cell-containing sample is a blood sample, such as a blood cell lysate. Cell lysis may be accomplished by standard procedures. In certain embodiments, the cell-containing sample is a whole blood cell lysate.

In other embodiments, the cell-containing sample is a white blood cell lysate. Methods for obtaining white blood cells from blood are known in the art (Rickwood et al., *Anal. Biochem.*, 123:23-31 (1982); Fotino et al., *Ann. Clin. Lab. Sci.*, 1:131 (1971)). Commercial products useful for cell separation include without limitation Ficoll-Paque (Pharmacia Biotech) and NycoPrep (Nycomed). In some situations, white blood cell lysates provide better reproducibility of data than do whole blood cell lysates.

Variability in sample preparation of cell-containing samples can be corrected by normalizing the data by, for example, protein content or cell number. In certain embodiments, the sample may be normalized relative to the total protein content. Total protein content in the sample can be determined using standard procedures, including, without limitation, Bradford assay and the Lowry method.

Measuring Tyrosine Kinase Activity

In some embodiments, proteins are isolated from the acellular body fluid prior to further analysis. Proteins from samples can be isolated using techniques that are well-known to those of skill in the art. The protein isolation methods employed can, e.g., be including, but not limited to, e.g., those described in Harlow & Lane, *Antibodies: A Laboratory Manual* (Cold Spring Harbor Laboratory Press, Cold Spring Harbor, N.Y., 1988). In some embodiments, total protein is extracted from the acellular body fluid sample. Plasma purification methods are known in the art such. See e.g., Cohn, E. J., et al., *Am. Chem. Soc.*, 62:3396-3400.(1940); Cohn, E. J., et al., *J. Am. Chem. Soc.*, 72:465-474 (1950); Pennell, R. B., Fractionation and isolation of purified components by precipitation methods, pp. 9-50. In *The Plasma Proteins*, Vol. 1, F. W. Putman (ed.). Academic Press, New York (1960); and U.S. Pat. No. 5,817,765.

Assays for measuring kinase activity are well known in the art depending on the particular kinase. Specific assay protocols are available in standard sources known to the ordinarily skilled artisan. For example, see "Kinases" in Ausubel et al., eds. (1994-1998) Current Protocols in Molecular Biology and references cited therein.

In one embodiment, the TK assay is performed using the Universal Tyrosine Kinase Assay Kit (GenWay Biotech, San Diego, Calif.). Briefly, the universal protein tyrosine kinase substrate peptide, Poly (Glu-Tyr) (4:1, 20-50 kDa), is pre-coated onto 96-well microtiter plates. Serial dilutions of prepared 5-point standards (with known TK activities) and plasma (1:100 dilution) or serum samples are added to the plate in triplicate along with an ATP-containing kinase buffer. After incubation at 37° C. for 30 min to allow phosphorylation of tyrosine residues, the sample solution is removed and the wells are washed with Washing buffer (PBS with 0.05% Tween-20) and blocked with Blocking reagent. Anti-phosphotyrosine (PY20)-horseradish peroxidase (HRP) conjugate is then added to the plate. After incubation at 37° C. for 30 min, the PY20-HRP solution is replaced by HRP substrate solution (TMBZ). For colorimetric determination of cTK activity, the sample's specific absorbance at 450 nm is calculated from a standard curve.

Diagnosis of Disease States

In some embodiments, the cTK activity level in a test sample is used to diagnose a disease. The activity level may be compared to a reference value to determine if the levels of cTK activity are elevated or reduced relative to the reference value. Typically, the reference value is the cTK activity measured in a comparable sample from one or more healthy individuals. An increase or decrease in the cTK activity may be used in conjunction with clinical factors other than cTK activity to diagnose a disease.

Association between a pathological state (e.g., a proliferative hematological disorder) and the aberration of a cTK activity level can be readily determined by comparative analysis in a normal population and an abnormal or affected population. Thus, for example, one can study the cTK activity level in both a normal population and a population affected with a particular pathological state. The study results can be compared and analyzed by statistical means. Any detected statistically significant difference in the two populations would indicate an association. For example, if the cTK activity is statistically significantly higher in the affected population than in the normal population, then it can be reasonably concluded that higher cTK activity is associated with the pathological state. Conversely, if the cTK activity is not statistically significantly higher in a test population than in the normal population, then it can be reasonably concluded that the test population does not have the pathological state.

Statistical methods can be used to set thresholds for determining when the cTK activity level in a subject can be considered to be different than or similar to a reference level. In addition, statistics can be used to determine the validity of the difference or similarity observed between a patient's specific activity level and the reference level. Useful statistical analysis methods are described in L. D. Fisher & G. vanBelle, *Biostatistics: A Methodology for the Health Sciences* (Wiley-Interscience, NY, 1993). For instance, confidence ("p") values can be calculated using an unpaired 2-tailed t test, with a difference between groups deemed significant if the p value is less than or equal to 0.05. As used herein a "confidence interval" or "CI" refers to a measure of the precision of an estimated or calculated value. The interval represents the range of values, consistent with the data that is believed to encompass the "true" value with high probability (usually 95%). The confidence interval is expressed in the same units as the estimate or calculated value. Wider intervals indicate lower precision; narrow intervals indicate greater precision. Suitable confidence intervals of the invention are 90%, 95%, 97.5%, 98%, 99%, 99.5%, 99.9% and 99.99%. A "p-value" as used herein refers to a measure of probability that a difference between groups happened by chance. For example, a difference between two groups having a p-value of 0.01 (or p=0.01) means that there is a 1 in 100 chance the result occurred by chance. Suitable p values are 0.1, 0.05, 0.025, 0.02, 0.01, 0.005, 0.001, and 0.0001. Confidence intervals and p-values can be determined by methods well-known in the art. See, e.g., Dowdy and Wearden, *Statistics for Research*, John Wiley & Sons, New York, 1983. Exemplary statistical tests for associating a prognostic indicator with a predisposition to an adverse outcome are described hereinafter. Once an association is established between cTK activity and a pathological state, then the particular physiological state can be diagnosed or detected by determining whether a patient has the particular aberration, i.e. elevated or reduced cTK activity levels. Moreover, a "normal" cTK activity would indicate the patient does not have the particular aberration.

The term "elevated levels" or "higher levels" as used herein refers to levels of a cTK activity that are higher than what would normally be observed in a comparable sample from control or normal subjects (i.e., a reference value). In some embodiments, "control levels" (i.e., normal levels) refer to a range of cTK activity levels that would normally be expected to be observed in a mammal that does not have a proliferative hematological disorder. A control level may be used as a reference level for comparative purposes. "Elevated levels" refer to cTK activity levels that are above the range of control levels. The ranges accepted as "elevated levels" or "control levels" are dependent on a number of factors. For example, one laboratory may routinely determine the cTK activity in a sample that is different than the cTK activity obtained for the same sample by another laboratory. Also, different assay methods may achieve different value ranges. Value ranges may also differ in various sample types, for example, different body fluids or by different treatments of the sample. One of ordinary skill in the art is capable of considering the relevant factors and establishing appropriate reference ranges for "control values" and "elevated values" of the present invention. For example, a series of samples from control subjects and subjects diagnosed with proliferative hematological disorders can be used to establish ranges that are "normal" or "control" levels and ranges that are "elevated" or "higher" than the control range.

Similarly, "reduced levels" or "lower levels" as used herein refer to levels of cTK activity that are lower than what would normally be observed in a comparable sample from control or normal subjects (i.e., a reference value). In some embodiments, "control levels" (i.e. normal levels) refer to a range of cTK activity levels that would be normally be expected to be observed in a mammal that does not have a proliferative hematological disorder and "reduced levels" refer to cTK activity levels that are below the range of such control levels.

For example, elevated cTK activity as compared to the corresponding reference values from healthy individuals are associated with the presence of CML and ALL. While an elevation in cTK activity alone may not provide a conclusive diagnosis, the information is useful in conjunction with clinical factors other than cTK activity commonly used in the diagnosis of, for example, leukemia; the cTK activity then provides a further factor in confirming a diagnosis. Clinical factors of particular relevance in the diagnosis of proliferative hematological disorders include, but are not limited to, the patient's medical history, a physical examination of the patient, complete blood count, examination of bone marrow cells, cytogenetics, and immunophenotyping of blood cells.

Monitoring Progression and/or Treatment

In one aspect, the cTK activity level in a biological sample of a patient is used to monitor the effectiveness of treatment or the prognosis of disease. In some embodiments, the cTK activity level in a test sample obtained from a treated patient can be compared to the level from a reference sample obtained from that patient prior to initiation of a treatment. Clinical monitoring of treatment typically entails that each patient serve as his or her own baseline control. In some embodiments, test samples are obtained at multiple time points following administration of the treatment. In these embodiments, measurement of cTK activity level in the test samples provides an indication of the extent and duration of in vivo effect of the treatment.

A prognosis may be expressed as the amount of time a patient can be expected to survive. Alternatively, a prognosis may refer to the likelihood that the disease goes into remission or to the amount of time the disease can be expected to remain in remission. Prognosis can be expressed in various ways; for example, prognosis can be expressed as a percent chance that a patient will survive after one year, five years, ten years or the like. Alternatively, prognosis may be expressed as the number of years, on average that a patient can expect to survive as a result of a condition or disease. The prognosis of a patient may be considered as an expression of relativism, with many factors affecting the ultimate outcome. For example, for patients with certain conditions, prognosis can be appropriately expressed as the likelihood that a condition may be treatable or curable, or the likelihood that a disease will go into remission, whereas for patients with more severe conditions prognosis may be more appropriately expressed as likelihood of survival for a specified period of time.

Additionally, a change in a clinical factor from a baseline level may impact a patient's prognosis, and the degree of change in level of the clinical factor may be related to the severity of adverse events. Statistical significance is often determined by comparing two or more populations, and determining a confidence interval and/or a p value.

Multiple determinations of cTK activity levels can be made, and a temporal change in activity can be used to determine a prognosis. For example, comparative measurements are made of the cTK activity of an acellular body fluid in a patient at multiple time points, and a comparison of a cTK activity value at two or more time points may be indicative of a particular prognosis. A prognosis is often determined by examining one or more clinical factors and/or symptoms that correlate to patient outcomes. As described herein, the cTK activity level is a clinical factor useful in determining prognosis. The skilled artisan will understand that associating a clinical factor with a predisposition to an adverse outcome may involve statistical analysis.

In certain embodiments, the levels of cTK activity are used as indicators of an unfavorable prognosis. According to the method, the determination of prognosis can be performed by comparing the measured cTK activity level to levels determined in comparable samples from healthy individuals or to levels known to corresponding with favorable or unfavorable outcomes. The absolute cTK activity levels obtained may depend on any number of factors, including, but not limited to, the laboratory performing the assays, the assay methods used, the type of body fluid sample used and the type of disease a patient is afflicted with. According to the method, values can be collected from a series of patients with a particular disorder to determine appropriate reference ranges of cTK activity for that disorder. One of ordinary skill in the art is capable of performing a retrospective study that compares the determined cTK activity levels to the observed outcome of the patients and establishing ranges of levels that can be used to designate the prognosis of the patients with a particular disorder. For example, cTK activity levels in the lowest range would be indicative of a more favorable prognosis, while cTK activity levels in the highest ranges would be indicative of an unfavorable prognosis. Thus, in this aspect the term "elevated levels" refers to levels of cTK activity that are above the range of the reference value. In some embodiments patients with "high" or "elevated" cTK activity levels have levels that are higher than the median activity in a population of patients with that disease. In certain embodiments, "high" or "elevated" cTK activity levels for a patient with a particular disease refers to levels that are above the median values for patients with that disorder and are in the upper 40% of patients with the disorder, or to levels that are in the upper 20% of patients with the disorder, or to levels that are in the upper 10% of patients with the disorder, or to levels that are in the upper 5% of patients with the disorder.

Because the level of cTK activity in a test sample from a patient typically relates to the prognosis of a patient in a continuous fashion, the determination of prognosis can be performed using statistical analyses to relate the determined cTK activity levels to the prognosis of the patient. A skilled artisan is capable of designing appropriate statistical methods. For example, the methods may employ the chi-squared test, the Kaplan-Meier method, the log-rank test, multivariate logistic regression analysis, Cox's proportional-hazard model and the like in determining the prognosis. Computers and computer software programs may be used in organizing data and performing statistical analyses.

In certain embodiments, the prognosis of ALL, AML, CLL, or MDS patients can be correlated to the clinical outcome of the disease using the cTK activity level and other clinical factors. Simple algorithms have been described and are readily adapted to this end. The approach by Giles et. al., *British Journal of Hemotology*, 121:578-585, is exemplary. As in Giles et al., associations between categorical variables (e.g., cTK activity levels and clinical characteristics) can be assessed via crosstabulation and Fisher's exact test. Unadjusted survival probabilities can be estimated using the method of Kaplan and Meier. The Cox proportional hazards regression model also can be used to assess the ability of patient characteristics (such as cTK activity levels) to predict survival, with 'goodness of fit' assessed by the Grambsch-Therneau test, Schoenfeld residual plots, martingale residual plots and likelihood ratio statistics (see Grambsch et al, 1995). In some embodiments, this approach can be adapted as a simple computer program that can be used with personal computers or personal digital assistants (PDA). The prediction of patients' survival time in based on their cTK activity levels can be performed via the use of a visual basic for applications (VBA) computer program developed within Microsoft® Excel. The core construction and analysis may be based on the Cox proportional hazard models. The VBA application can be developed by obtaining a base hazard rate and parameter estimates. These statistical analyses can be performed using a statistical program such as the SAS® proportional hazards regression, PHREG, procedure. Estimates can then be used to obtain probabilities of surviving from one to 24 months given the patient's covariates. The program can make use of estimated probabilities to create a graphical representation of a given patient's predicted survival curve. In certain embodiments, the program also provides 6-month, 1-year and 18-month survival probabilities. A graphical interface can be used to input patient characteristics in a user-friendly manner.

In some embodiments, multiple prognostic factors, including cTK activity level, are considered when determining the prognosis of a patient. For example, the prognosis of an AML, ALL, CLL, or MDS patient may be determined based on cTK activity and one or more prognostic factors selected from the group consisting of cytogenetics, performance status, AHD (antecedent hematological disease), age, and diagnosis (e.g., MDS v. AML). In certain embodiments, other prognostic factors may be combined with the specific activity level in the algorithm to determine prognosis with greater accuracy.

Cytogenetics refers to the analysis of the physical appearance of chromosomes (e.g., the number and shape of the chromosomes). The identification of particular chromosome alterations or abnormalities can be helpful in diagnosing, for example, specific types of leukemia and lymphoma. Furthermore, particular types of chromosomal alterations have been associated with clinical behavior or response to therapy and therefore can be used in determining treatment approaches. For example, patients with AML are assigned to one of several risk categories (i.e., good, intermediate, bad, and very bad) based on the appearance of metaphase chromosomes according to the International System for Cytogenetic Nomenclature (ISCN). Thus, in AML, patients in the good-risk category or having good cytogenetics exhibit t(8;21) or inv16; intermediate-risk or intermediate cytogenetics exhibit a normal karyotype (NN) or -Y only; the bad-risk category or bad cytogenetics include all other abnormalities, without good and very bad cytogenetic features; and very bad risk -5, 5-, -7, 7q-, complex abnormalities (i.e., clones with a number of unrelated abnormalities), abnormal (abn) 3q, t(9;22), t(6;9), or abn 11q23 and absence of good cytogenetic features. For example, AML patients having good cytogenetics or in the good-risk category are treated with chemotherapy, while patients having bad or very bad cytogenetics or are in the highest risk categories are treated with bone marrow transplants. However, approximately half of AML patients have "normal" cytogenetics and therefore fall into an intermediate risk group, wherein the treatment and the response thereto can vary considerably (Marcucci et al., *Curr Opin Hematol,* 12(1):68-75, 2005).

Predicting Response to Therapy

In one aspect, the cTK activity level in a patient sample can be used to predict response to therapy for patients having a proliferative hematological disorder. The methods (also referred to herein as a "screening assay") can be used for identifying modulators, i.e., candidate or test compounds or agents, such as tyrosine kinase inhibitors (TKI), that exhibit a stimulatory or inhibitory effect on, for example, kinase activity. The test compounds or agents may be e.g., antibodies, peptides, peptidomimetics, small molecules, or other drugs.

The test compounds can be obtained using any of the numerous approaches in combinatorial library methods known in the art, including biological libraries, spatially-addressable parallel solid phase or solution phase libraries, synthetic library methods requiring deconvolution, the "one-bead one-compound" library method, and synthetic library methods using affinity chromatography selection. The biological library approach is limited to peptide libraries, while the other four approaches are applicable to peptide, nonpeptide oligomer, or small molecule libraries of compounds.

In one embodiment, an assay is a cell-free assay comprising contacting an acellular body fluid sample from a patient with a test compound and determining the ability of the test compound to modulate (e.g., stimulate or inhibit) the activity of the cTK. Determining the ability of the test compound to modulate the activity of a cTK can be accomplished, for example, by determining the ability of the kinase protein to further modulate a kinase substrate. For example, the catalytic/enzymatic activity of the target molecule on an appropriate substrate can be determined as described above.

Agents or modulators that have a stimulatory or inhibitory effect on kinase activity as identified by a screening assay described herein, can be administered to individuals to treat disorders associated with aberrant kinase activity as well as to modulate the cellular growth, differentiation and/or metabolism. In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the cTK activity in an individual can be determined to thereby select appropriate agent(s) for therapeutic or prophylactic treatment of the individual.

Kits

A kit may be used for conducting the diagnostic and prognostic methods described herein. Typically, the kit should contain, in a carrier or compartmentalized container, reagents useful in any of the above-described embodiments of the diagnostic method. The carrier can be a container or support, in the form of, e.g., bag, box, tube, rack, and is optionally compartmentalized. The carrier may define an enclosed confinement for safety purposes during shipment and storage. In one embodiment, the kit includes a synthetic substrate for a protein kinase and an antibody selectively immunoreactive with a phosphorylated tyrosine. The antibodies may be labeled with a detectable marker such as radioactive isotopes, or enzymatic or fluorescence markers. Alternatively, secondary antibodies such as labeled anti-IgG and the like may be included for detection purposes. Optionally, the kit can include standard tyrosine kinases prepared or purified for comparison purposes. Instructions for using the kit or reagents contained therein are also included in the kit.

EXAMPLES

The present methods and kits, thus generally described, will be understood more readily by reference to the following examples, which are provided by way of illustration and are not intended to be limiting of the present methods and kits. The following is a description of the materials and experimental procedures used in the example.

Example 1—Circulating Tyrosine Kinase Biomarkers in CML and ALL

Materials and Methods

Patient Samples.

Peripheral blood samples were obtained from patients with newly-diagnosed CML (n=46), multidrug-resistant CML (n=24), or BCR-ABL1-positive ALL (n=24), as well as 38 healthy individuals. All patient and normal samples were collected with signed informed consent in accordance with an Institutional Review Board (IRB)-approved protocol. The diagnoses of CML and BCR-ABL1 ALL were confirmed by routine karyotyping and fluorescence in situ hybridization (FISH) studies. Blood samples were centrifuged and the separated plasma or serum was kept frozen until the time of analysis.

Measurement of cTK Activity.

The TK assay was performed using the Universal Tyrosine Kinase Assay Kit (GenWay Biotech, San Diego, Calif.) according to the manufacturer's instructions with some modifications. The universal protein tyrosine kinase substrate peptide, Poly (Glu-Tyr) (4:1, 20-50 kDa), was pre-coated onto 96-well microtiter plates. Serial dilutions of prepared 5-point standards (with known TK activities) and plasma (1:100 dilution) or serum samples were added to the plate in triplicate along with an ATP-containing kinase buffer. After incubation at 37° C. for 30 min to allow phosphorylation of tyrosine residues, the sample solution was removed and the wells were washed with washing buffer (PBS with 0.05% Tween-20) and blocked with Blocking reagent. Anti-phosphotyrosine (PY20)-horseradish peroxidase (HRP) conjugate was then added to the plate. After incubation at 37° C. for 30 min, the PY20-HRP solution was replaced by HRP substrate solution (TMBZ). For colorimetric determination of cTK activity, the sample's specific absorbance at 450 nm was calculated from the standard curve.

Quantification of BCR-ABL1 Expression.

Quantitative measurement of BCR-ABL1 transcript level was performed as described in Ma et al. (18). The two types of BCR-ABL1 fusion transcripts (b2a2/b3a2 and e1a2) were quantitated in a single real-time RT-PCR using the native ABU transcript as an internal reference. The results were reported as ratios of the quantities of the fused BCR-ABL1 to the ABU internal control mRNA.

Analysis of CRKL and STAT-5 Phosphorylation by Quantitative Flow Cytometry.

Immunostaining and flow cytometry analysis of BCR-ABL1 downstream effector proteins were performed as described in Jilani et al. (19). Washed whole blood samples were fixed with formaldehyde, permeabilized with a PBS-buffered saponin-based permeabilizing solution (IntraPrep Permeabilization kit, Beckman Coulter, Fullerton, Calif.), and incubated with primary antibodies directed against p-CRKL (Tyr207) or p-STAT-5 (Tyr694) (Cell Signaling Technologies, Beverly, Mass.). A PE-conjugated goat anti-rabbit IgG secondary antibody (Santa Cruz Biotechnology, Santa Cruz, Calif.) was then used for detection, followed by fluorescence analysis with a FACSCalibur flow cytometer (Becton Dickinson, Franklin Lakes, N.J.).

Ex Vivo Studies of the Effects of TKIS on Plasma cTK Activity.

Imatinib and dasatinib were purchased from LC Laboratories (Woburn, Mass.). Stock solutions of imatinib and dasatinib (100 mmol/L) were prepared in DMSO and stored at −20° C. Imatinib and dasatinib was added directly to the diluted plasma samples at final concentrations ranging between 0.05 and 25 μmol/L, corresponding to plasma concentrations in patients receiving these agents (16, 20). The ATP concentration in each kinase reaction was kept at 0.4 mmol/L. The reactants were then subjected to in vitro TK activity analysis as described above.

Statistical Analysis.

Relationships between continuous variables were assessed with Spearman rank correlations. Representative data were derived from at least three independent experiments. Statistical comparisons between different groups were performed using unpaired Student's t-test. P values <0.05 were considered statistically significant.

Results

Direct Detection of Circulating Tyrosine Kinase (cTK) Activity in Human Plasma and Serum.

Figure 1B:
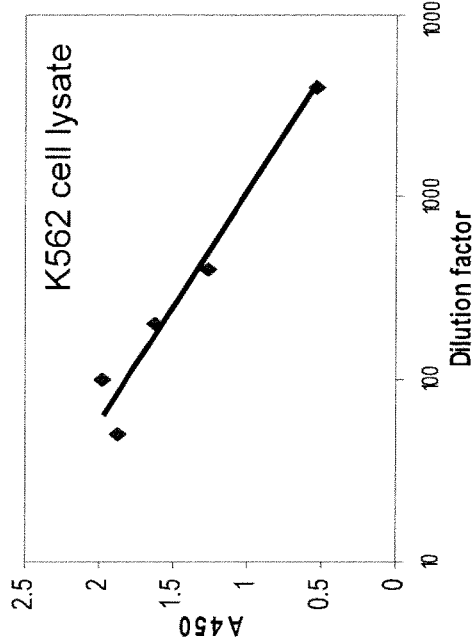
Figure 1C:
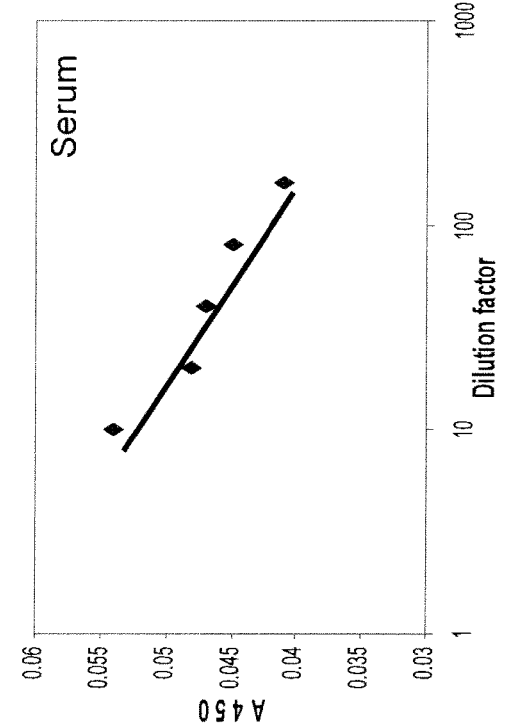

Using a chromogenic universal TK assay kit, we measured cTK activity directly from plasma and sera as well as K562 CML cell lysate. Samples and standards were added into 96-well microtiter plates on which synthesized poly (Glu-Tyr) peptide substrates had been immobilized. Specific cTK activity was quantified by spectrophotometry. To ensure that the dynamic range of this assay would encompass the range of high and low cTK activities found in different sample types, we first measured kinase activities following serial dilution of samples. FIG. 1 demonstrates a linear relationship between cTK activities and sample concentrations in plasma, serum, or K562 lysates. Baseline cTK activity was approximately 100-fold higher in plasma than in paired serum samples. Our results show that circulating TK activity is in a cell-free soluble fraction and is readily detectable from plasma/serum without pre-cleaning, fractionation, or enrichment steps.

Elevated Plasma cTK Activity in Newly Diagnosed CML and BCR-ABL1-Positive ALL Patients.

Constitutively active BCR-ABL1 kinase and its downstream signaling events are predominant TKs in CML and BCR-ABL1-positive ALL. We therefore examined whether plasma cTK activity is elevated in patients with these diseases relative to normal control subjects. Plasma cTK activity was ~8-10-fold higher in BCR-ABL1-positive ALL and CML patients than in control subjects. The median cTK activities were 659.55 U/mL (n=24, range 0-1626.90 U/mL) for Ph+ ALL patients, 801.93 U/mL (n=46, range 18.10-3932.30 U/mL) for CML patients, and 82.85 U/mL (n=38, range 0.63-852.80 U/mL) for control subjects (each P<0.001 vs control group; Table 1). This finding indicates that TK can be released from tumor cells and be detected at elevated levels in plasmas of BCR-ABL1-positive leukemia patients.

TABLE 1

Higher cTK activity in plasma of patients with BCR-ABL1-positive leukemia

|  | CML | Ph+ ALL | Normal |
| --- | --- | --- | --- |
| Sample No. | 46 | 24 | 38 |
| Median, U/mL | 801.93 | 659.55 | 82.85 |
| Mean, U/mL | 1149.55 | 616.70 | 155.88 |
| Range, U/mL | 18.10-3932.30 | 0-1626.90 | 0.63-852.80 |
| P value* | <0.001 | <0.001 | — |

CML, chronic myelogenous leukemia; ALL, acute lymphocytic leukemia.

*P value was determined by Student's t-test as compared to the Normal control.

We next used two different approaches to evaluate the association of cTK activity with a series of cellular BCR-ABL1 parameters. The results of quantitative flow cytometry demonstrated significant correlation of plasma cTK activity with phospho-CRKL (P<0.001) and phospho-STAT-5 levels (P=0.003), both of which are direct downstream targets of BCR-ABL1 kinase activation (Table 2). However, plasma cTK activity did not correlate with BCR-ABL1 transcript levels by real-time RT-PCR (P=0.634) and was independent of BCR-ABL1 mutation type. These results demonstrate that plasma cTK activity is a reliable surrogate marker of cellular BCR-ABL1 kinase activation.

TABLE 2

Spearman correlations of cTK activity with BCR-ABL1 molecular parameters*

|  | Plasma cTK activity | |
| --- | --- | --- |
|  | Spearman | P value |
| Cellular p-CRKL level (Quantitative flow cytometry) | 0.66 | 0.0005 |
| Cellular p-STAT-5 level (Quantitative flow cytometry) | 0.58 | 0.003 |
| BCR-ABL1/ABL1 mRNA ratio (real-time RT-PCR) | 0.09 | 0.634 |

*Correlation analysis was performed using 24 multidrug-resistant CML cases (median cTK activity = 202.18 U/mL; range = 17.00-1214.91 U/mL) with available BCR-ABL1 cellular data.

Universal TK Activity is a Good Response Indicator for BCR-ABL1-Targeted Drugs.

To further test the suitability of this universal TK activity assay for BCR-ABL1 kinase activation and its targeted drug response, we developed a cell model reflecting these conditions by transfecting K562 cells, which constitutively express BCR-ABL1, with expression vector containing wild-type (control) or drug-resistant mutant BCR-ABL1 cDNA, and exposed the transformed cells to the two TKIs individually. Lysates from K562 cells overexpressing the BCR-ABL1 mutant (35-nt INS) showed higher TK activity (i.e., more resistant) after imatinib (1.2 uM) or dasatinib (5 nM) treatment as compared to wild-type and empty vector control (Table 3), in accordance with previous reports (21, 22). Our observation indicates that the TK activity measured here reflects the dominant population of drug-targeted BCR-ABL1 and its associated signaling TKs.

TABLE 3

Universal TK activity is a good response indicator
in drug-treated BCR-ABL1-transfected K562 cells

| | Relative TK activity, % | | |
|---|---|---|---|
| | Empty vector | Wild type BCR-ABL1 | Mutant (35-nt INS) BCR-ABL1 |
| Vehicle only | 100 | 100 | 100 |
| Imatinib (1.2 µM) | 57.3 | 87.7 | 100 |
| Dasatinib (5 nM) | 15.6 | 20.6 | 42.7 |

TK activity was normalized to the no-drug control (vehicle). Representative data were expressed as percent activity relative to the control (set as 100) in each group. K562 cells that had been transfected with empty vector, wild type or 35-nt INS mutant BCR-ABL1 vector were exposed to vehicle, imatinib, or dasatinib at the indicated concentrations.

Effects of Imatinib and Dasatinib on Plasma cTK Activity—An Ex Vivo Study.

Next we assessed the efficacy of imatinib and dasatinib against BCR-ABL1-positive plasma from a CML patient in an ex vivo model. Patient plasma was exposed to imatinib or dasatinib at concentrations of 2 or 0.4 mM before TK activity measurement. Each of these TKIs caused a concentration-dependent reduction of cTK activity, with a more profound effect by dasatinib at each concentration (Table 4). These results indicate that BCR-ABL1 TK is constitutively activated and released into circulation. The inhibition of cTK activation ex vivo by the potent ABL1 TKIs imatinib and dasatinib further supports cTK activity as a real-time response indicator for BCR-ABL1-targeted therapy.

TABLE 4

Plasma cTK activity is a real-time indicator
of drug response in ex vivo assay

| | Relative cTK activity, % | |
|---|---|---|
| | Drug concentration 2 mM | Drug concentration 0.4 mM |
| Vehicle only | 100 | 100 |
| Imatinib | 92.3 | 93.6 |
| Dasatinib | 54.0 | 77.0 |

Plasma from a CML patient was exposed directly to 2 different concentrations of vehicle, imatinib, or dasatinib. cTK activity was normalized to the no-drug control (vehicle). The ATP concentration in this kinase reaction was 1.67 mM. Representative data are expressed as percent activity relative to the control (set at 100) in each group.

Effect of TKIS on cTK Activity in Plasma from a CML Patient with the T315I Mutation.

Figure 2A:
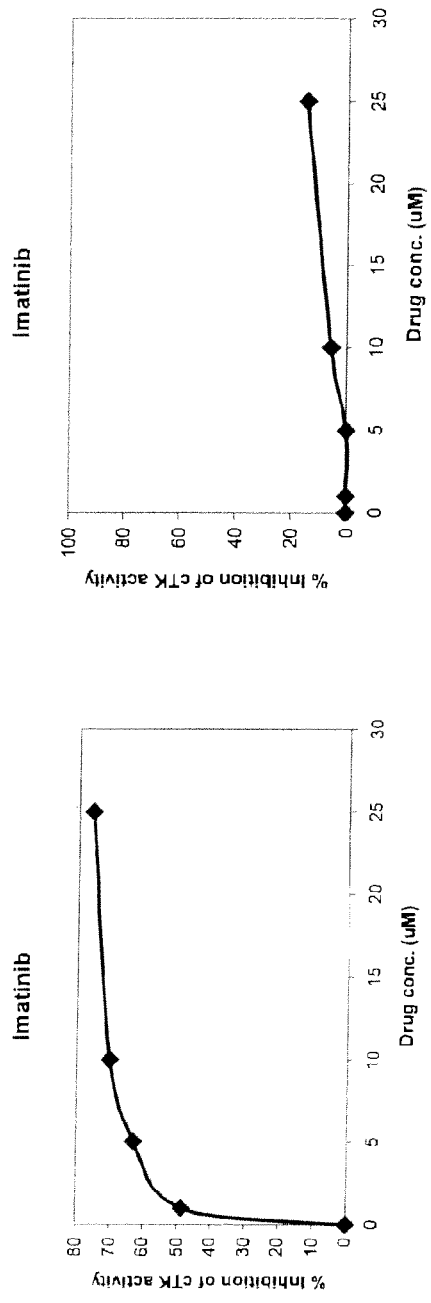
FIGS. 2A-2B show that ex vivo cTK activity is a good response indicator for imatinib and dasatinib. Concentration-response is shown by the representative inhibition curves.
Figure 2A:
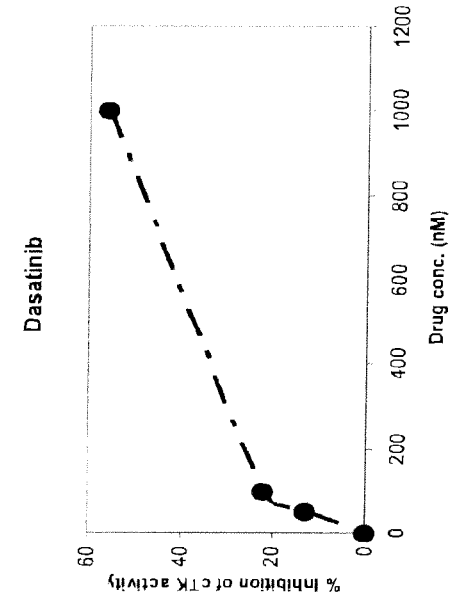
Figure 2A:
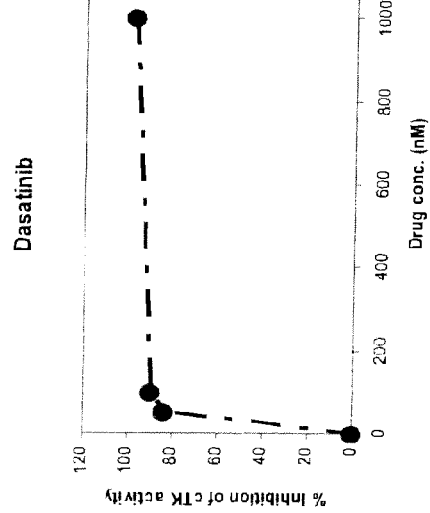

It has been shown that on day 1 after oral administration at doses of 400 mg to 500 mg bid, the mean plasma trough concentrations of imatinib range from 1000 to 3500 ng/mL (~2-6 µM), and drug accumulation increases with repeated once-daily dosing (20). For dasatinib, the achievable plasma trough concentration is about 100 nM. To consolidate our findings to reflect physiological conditions and the pharmacokinetic distribution of the drugs, we incubated plasma samples from a newly diagnosed and a multidrug-resistant CML patient (with T315I mutation) with imatinib or dasatinib at concentrations of 1.0, 5.0, 10, or 25 µM. Dasatinib was also tested at 50 nM and 100 nM. cTK activity was then quantified. Analysis of the inhibition curves revealed that both drugs effectively inhibited cTK activity for the patient with newly diagnosed CML ($IC_{50}$<1 µM). Plasma from the CML patient harboring the T315I mutation showed little inhibition with imatinib but good inhibition with dasatinib (i.e., 1-5 µM imatinib and 50-100 nM dasatinib) (FIG. 2A). The results of this ex vivo cTK activity assay suggest that dasatinib at higher doses could be a reasonable second-line choice for this particular patient.

Expression Levels of BCR-ABL1 35-NT Inseriton Mutation and Drug Resistance.

Figure 2B:
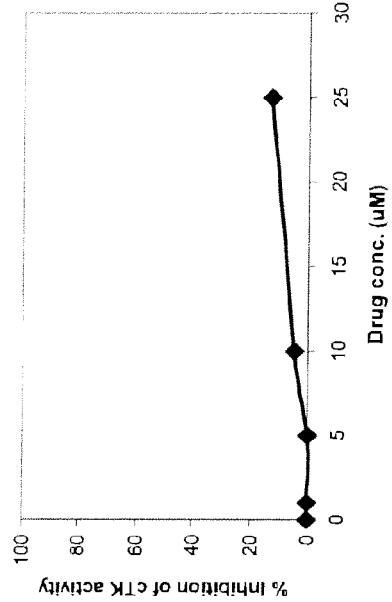
Figure 2B:
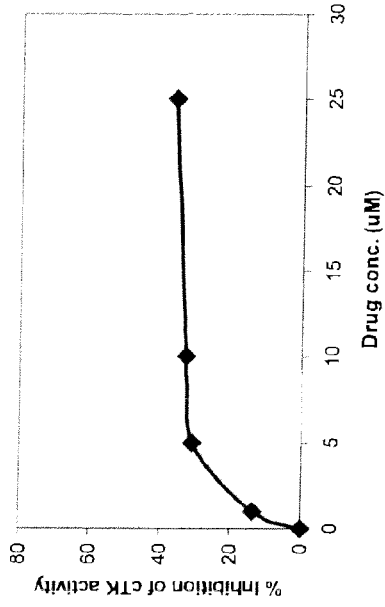
Figure 2B:
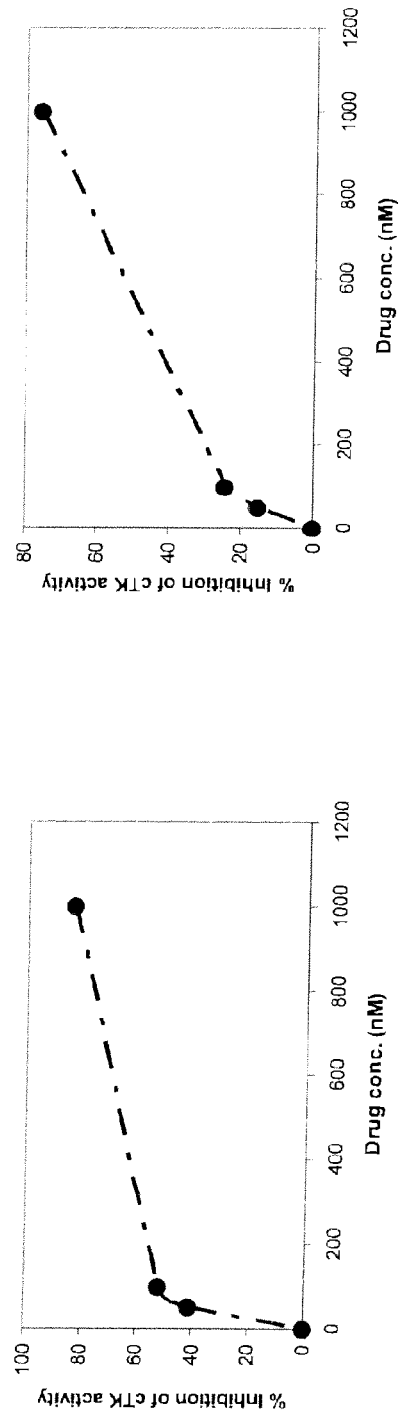

Imatinib-resistant CML patients express varying levels of the alternatively spliced BCR-ABL1 35-nt INS mRNA (21, 22). This variation alters imatinib binding to BCR-ABL1 in a way similar to that of the T315I mutation (21), a well-established cause of imatinib resistance. To test whether the effects of 35-nt INS depend on its expression level, we explored the effects of TKIs on plasma from two patients expressing different levels of 35-nt INS transcript (10% or 35%). Imatinib resistance was much higher in plasma from the patient with high-level expression (35%) of the 35-nt INS mutant than in plasma from the patient with lower-level expression (FIG. 2B). Although plasma from both patients showed strong inhibition by dasatinib at concentrations greater than 1 µM, concentrations of 50 and 100 nM showed only marginal inhibition. These results are consistent with the previous report (21) that imatinib resistance conferred by 35-nt INS is dependent on its expression level, and further support the clinical utility of this ex vivo cTK activity assay.

Discussion

The findings of this study establish that cTK activity can be easily, directly, and linearly detected from human plasma and serum without a pre-cleaning, fractionation, or enrichment step. cTK activity was much higher in plasma than in serum, a difference that might be attributable to loss on entrapment of TKs from circulation during clotting.

Our results indicate a relationship between plasma cTK activity and the biological activity of BCR-ABL1 in Philadelphia chromosome-positive patients. Leukemia patients with constitutive BCR-ABL1 activation commonly have high levels of plasma cTK activity. Although the employed peptide substrate is not specific and can be recognized by various TKs such as ABL1, ZAP-70, c-Src, FAK, EGFR etc, several lines of evidence suggest that the majority of signals detected by this system in our samples came from BCR-ABL1 and the associated signaling TKs. First, plasma cTK activity correlated strongly with cellular p-CRKL and p-STAT-5 levels, both of which are main downstream effectors for BCR-ABL1 activation. Second, detectable TK activity, either endogenous or forced BCR-ABL1 overexpression in the K562 cell line, showed a concentration-dependent response to imatinib and dasatinib, two selective inhibitors of BCR-ABL1 and related TKs. Third, plasma cTK activity appeared to be a reliable drug response indicator for BCR-ABL1-targeted treatment in a series of ex vivo studies. Finally, detectable cTK activity responded perfectly to imatinib and dasatinib at physiologically relevant plasma concentrations. This suggests that the plasma system has the potential to be used in TKI sensitivity screening and therapy selection.

Plasma cTK activity was markedly lower in multidrug-resistant CML than in patients with newly diagnosed CML (median: 202.18 U/mL vs. 801. 93 U/mL), consistent with recent findings from cell-based flow cytometry studies showing that resistant patients have significantly lower levels of BCR-ABL1, CRKL, and AKT phosphorylation than previously untreated patients (19). It is noteworthy that plasma cTK activity is independent of the ABL1 mutation type tested: point mutation T315I, E255K, Y253F, M244V, M351I or double mutation V299L/F486S or triple mutation M244V/E355G/L387M. The lack of correlation of plasma cTK activity with BCR-ABL1 transcript level was not surprising, as baseline levels of BCR-ABL1 transcript have been reported not to correlate with the percentage of p-CRKL or the $IC_{50}$ of imatinib (17).

The development of effective therapies against treatment-resistant CML will likely rely heavily on the early identification of potential responders. The success depends, at least in part, on the efficient application of periodic ex vivo cTK activity screening in the clinic. The plasma cTK activity measurement described here provides a reliable real-time disease and therapy monitoring tool and may be used for better management of patients with CML and BCR-ABL1-positive ALL being treated with TKIs. In addition, the same approach to be used in patients with other cancers, including solid tumors, in which access to the tumor tissue is difficult or impossible. If these patients are being treated with TKIs, the plasma cTK activity assay is a practical approach for testing drug sensitivity and monitoring disease and response to current therapy.

REFERENCES

1. Schlessinger J. Signal transduction: Autoinhibition control. Science 2003; 300:750-752.
2. Schlessinger J, Lemmon M A. Nuclear signaling by receptor tyrosine kinases: the first robin of spring. Cell 2006; 127:45-8.
3. Schlessinger J. Cell signaling by receptor tyrosine kinases. Cell 2000; 103:211-225.
4. Vlahovic G, Crawford J. Activation of tyrosine kinases in cancer. The Oncologist 2003; 8:531-8.
5. Krause D S, Van Etten R A. Tyrosine kinases as targets for cancer therapy. N Engl J Med 2005; 353:172-187.
6. Ocana A, Serrano R, Calero R, Pandiella, A. novel tyrosine kinase inhibitors in the treatment of cancer. Current Drug Targets 2009; 10:575-576.
7. Zhang J, Yang P L, Gray N S. Targeting cancer with small molecule kinase inhibitors. Nat Rev Cancer 2009; 9:28-39.
8. Wong S, Witte O N. The BCR-ABL story: Bench to bedside and back Annu Rev Immunol 2004; 22:247-306.
9. McGary E C, Onn A, Mills L, Heimberger A, Eton O, Thomas G W, et al. Imatinib mesylate inhibits platelet-derived growth factor receptor phosphorylation of melanoma cells but does not affect tumorigenicity in vivo. J Invest Dermatol 2004; 122:400-405.
10. Okuda K, Weisberg E, Gilliland D G, Griffin J D. ARG tyrosine kinase activity is inhibited by STI571. Blood. 2001; 97:2440-2448.
11. Druker B J, Tamura S, Buchdunger E, Ohno S, Segal G M, Fanning S, et al. Effects of a selective inhibitor of the Abl tyrosine kinase on the growth of Bcr-Abl positive cells. Nat Med. 1996; 2:561-566.
12. Dewar A L, Cambareri A C, Zannettino A C, Miller B L, Doherty K V, Hughes T P, et al. Macrophage colony stimulating factor receptor, c-fms, is a novel target of imatinib. Blood. 2005; 105:3127-3132.
13. Druker B J, Guilhot F, O'Brien S G, Gathmann I, Kantarjian H, Gattermann N, et al. Five-year follow-up of patients receiving imatinib for chronic myeloid leukemia. N Engl J Med 2006; 355:2408-2417.
14. Druker B J. STI571 (Gleevec™) as a paradigm for cancer therapy. Trends Mol Med 2002; 8:S14-S18.
15. Shah N P, Tran C, Lee F Y, Chen P, Norris D, Sawyers C L. Overriding imatinib resistance with a novel ABL kinase inhibitor. Science 2004; 305:399-401.
16. Talpaz M, Shah N P, Kantarjian H, Donato N, Nicoll J, Paquette R, et al. Dasatinib in imatinib-resistant Philadelphia chromosome-positive leukemias. N Engl J Med 2006; 354:2531-41.
17. White D, Saunders V, Lyons A B, Branford S, Grigg A, To L B, et al. In vitro sensitivity to imatinib-induced inhibition of ABL kinase activity is predictive of molecular response in patients with de novo CML. Blood 2005; 106:2520-2526.
18. Ma W, Tseng R, Gorre M, Jilani I, Keating M, Kantarjian H, et al. Plasma RNA as an alternative to cells for monitoring molecular response in patients with chronic myeloid leukemia. Haematol 2007; 92:170-175.
19. Jilani I, Kantarjian H, Gorre M, Cortes J, Ottmann O, Bhalla K, et al. Phosphorylation levels of BCR-ABL, CrkL, AKT and STAT5 in imatinib-resistant chronic myeloid leukemia cells implicate alternative pathway usage as a survival strategy. Leukemia Res 2008; 32:643-649.
20. Peng B, Hayes M, Resta D, Racine-Poon A, Druker B J, Talpaz M, et al. Pharmacokinetics and pharmacodynamics of imatinib in a phase I trial with chronic myeloid leukemia patients. J Clin Oncol 2004; 22:935-42.
21. Lee T-S, Ma W, Zhang X, Giles F, Cortes J, Kantarjian H, et al. BCR-ABL alternative splicing as a common mechanism for imatinib resistance: evidence from molecular dynamics simulations. Mol Cancer Ther 2008; 7:3834-41.
22. Ma W, Kantarjian H, Yeh C H, Zhang Z J, Cortes J, Albitar M. BCR-ABL truncation due to premature translation termination as a mechanism of resistance to kinase inhibitors. Acta Haematol 2009; 121:27-31.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

The inventions illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed is:

1. A method for measuring BCR-ABL1 kinase activity in a human subject having a BCR-ABL1-positive leukemia comprising:
   (a) contacting an acellular body fluid sample from a human subject having a BCR-ABL1-positive leukemia with a poly(Glu-Tyr) tyrosine kinase (TK) substrate;
   (b) detecting phosphorylation of the poly(Glu-Tyr) TK substrate by tyrosine kinases in the acellular body fluid sample to determine a circulating tyrosine kinase (cTK) activity level in the acellular sample; and
   (c) comparing the cTK activity level to a reference cTK activity level in a comparable sample from a healthy individual, wherein the difference in cTK activity is indicative of the level of BCR-ABL1 kinase activity in the subject, wherein BCR-ABL1-positive leukemia is selected from the group consisting of BCR-ABL1-positive chronic myelogenous leukemia (CML), chronic lymphocytic leukemia (CLL), acute myeloid leukemia (AML), and acute lymphoblastic leukemia (ALL) and the acellular body fluid sample is serum or plasma.

2. The method of claim 1, wherein the BCR-ABL1-positive leukemia is BCR-ABL1-positive chronic myelogenous leukemia (CML) or acute lymphoblastic leukemia (ALL).

3. The method of claim 1, wherein detecting the phosphorylation of the poly(Glu-Tyr) substrate is by contacting the substrate with a phospho-tyrosine-specific antibody.

4. The method of claim 1, further comprising contacting a second acellular body fluid sample from the human subject with a BCR-ABL1 inhibitor and determining the cTX activity level in the second acellular sample, wherein the second acellular body fluid sample is serum or plasma.

5. The method of claim 4, wherein the BCR-ABL1 inhibitor is imatinib or dasatinib.

* * * * *